(12) United States Patent
Lin

(10) Patent No.: US 7,013,714 B2
(45) Date of Patent: Mar. 21, 2006

(54) VISCOSITY MEASUREMENT APPARATUS

(75) Inventor: Yingjie Lin, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 46 days.

(21) Appl. No.: 10/675,000

(22) Filed: Sep. 30, 2003

(65) Prior Publication Data

US 2005/0066710 A1    Mar. 31, 2005

(51) Int. Cl.
    *G01N 25/00* (2006.01)
(52) U.S. Cl. .................................... 73/54.42; 73/54.01
(58) Field of Classification Search ............... 73/54.42, 73/54.01
    See application file for complete search history.

(56) References Cited

U.S. PATENT DOCUMENTS

| | | | |
|---|---|---|---|
| 4,466,275 A | 8/1984 | Thone | |
| 4,612,799 A | 9/1986 | Choi et al. | |
| 4,721,589 A * | 1/1988 | Harris | 264/40.1 |
| 5,616,855 A | 4/1997 | Ball | 73/54.43 |
| 6,083,399 A * | 7/2000 | Jameson et al. | 210/634 |
| 6,141,625 A | 10/2000 | Smith et al. | |
| 6,158,271 A | 12/2000 | de Corral | |
| 6,178,811 B1 | 1/2001 | Bonne et al. | |
| 6,405,579 B1 * | 6/2002 | Tjahjadi et al. | 73/54.11 |
| 6,571,608 B1 | 6/2003 | Shin et al. | |
| 6,673,622 B1 * | 1/2004 | Jina | 436/69 |
| 6,725,707 B1 * | 4/2004 | Lin et al. | 73/54.01 |
| 6,745,615 B1 * | 6/2004 | Kensey et al. | 73/54.04 |
| 6,810,718 B1 * | 11/2004 | Wilson et al. | 73/54.01 |

FOREIGN PATENT DOCUMENTS

CA    2107956 A    4/1995

* cited by examiner

*Primary Examiner*—Hezron Williams
*Assistant Examiner*—Rodney Frank
(74) *Attorney, Agent, or Firm*—Jimmy L. Funke

(57) ABSTRACT

A viscosity measurement apparatus, or viscometer, including a fluid flow channel, a heating element disposed at least around an exterior portion of the fluid flow channel near an inlet end, and a temperature sensor disposed within the fluid flow channel downstream from the heating element. The viscometer may also include a thermally insulating jacket disposed around the heating element and the fluid flow channel. A method of measuring viscosity with the viscometer includes immersing a fluid flow channel in the fluid, heating a portion of the fluid in the fluid flow channel near the inlet end of the fluid flow channel, and measuring a temperature of the fluid in the fluid flow channel at a position downstream from the inlet end of the fluid flow channel. The method further includes recording temperature changes of the fluid for a time period and comparing recorded temperature change characteristics to known fluid viscosities to determine viscosity.

13 Claims, 4 Drawing Sheets

VISCOSITY MEASUREMENT APPARATUS

BACKGROUND OF THE INVENTION

The present invention is generally related to viscometers, and, more particularly, to a viscometer for heating a fluid and measuring temperature variation of the fluid to determine viscosity.

Oil viscosity is an important physical parameter in many lubricant applications. For example, the viscosity of lubricants used in vehicles, such as engine oils and transmission oil, is one of the key parameters to determine oil quality and establish replacement intervals. A variety of viscosity measurement means have been developed for this purpose.

One known method of measuring viscosity of a fluid is to measure changes of behavior of system damping due to changes in the tested fluid's viscosity. A mechanical dynamic system, typically a vibration system, is used in this method. The mechanical system is immersed in the fluid to be tested and the system damping effect caused by the fluid can be measured and used to calculate a viscosity of the system. While this method works well in a laboratory environment, it does not appear to be suited for vehicle applications because of the complexity of the system and potential maintenance and serviceability problems. Other known viscometers use quartz crystal oscillators to measure viscosity of a fluid. The viscosity of the fluid affects the resonant frequency of the crystal and also causes a phase delay between an input and an output signal. These parameters can be monitored and measured to determine a viscosity of the tested fluid. However, such a test system may be expensive and difficult to package. Yet another way to measure viscosity is to heat the test fluid and measure the temperature variation of the fluid as the fluid moves in response to the heating. For example, it is known that a comparatively lower viscosity fluid will flow faster than a comparatively higher viscosity fluid when heated.

BRIEF SUMMARY OF THE INVENTION

Generally, the present invention fulfills the foregoing needs by providing in one aspect thereof a viscosity measurement system including a tubular flow guide for receiving a fluid at an inlet end and discharging the fluid at an outlet end. The system also includes a heating element positioned around an exterior portion of the tubular flow guide near an inlet end for heating the fluid entering the inlet end and a temperature sensor disposed within the fluid flow channel near the outlet end for measuring a temperature of the fluid proximate the sensor. The system may further include an insulating jacket disposed around the heating element and the fluid flow channel for reducing heat transfer between a portion of a fluid in the fluid flow channel and a portion of the fluid outside the fluid flow channel.

The present invention further fulfills the foregoing needs by providing in another aspect thereof, a method for measuring viscosity of a fluid including immersing a fluid flow channel in a fluid and heating a portion of the fluid in the fluid flow channel near an inlet end of the fluid flow channel. The method also includes measuring the temperature of the fluid in the fluid flow channel at a position downstream from the inlet end of the flow path. The method may further comprise recording temperature changes of the fluid for a time period and comparing the recorded temperature change characteristics to temperature change characteristics for known fluid viscosities to determine the viscosity of the fluid.

BRIEF DESCRIPTION OF THE DRAWINGS

The present invention will become apparent from the following detailed description of the invention when read with the accompanying drawings in which.

DETAILED DESCRIPTION OF THE INVENTION

Figure 1:
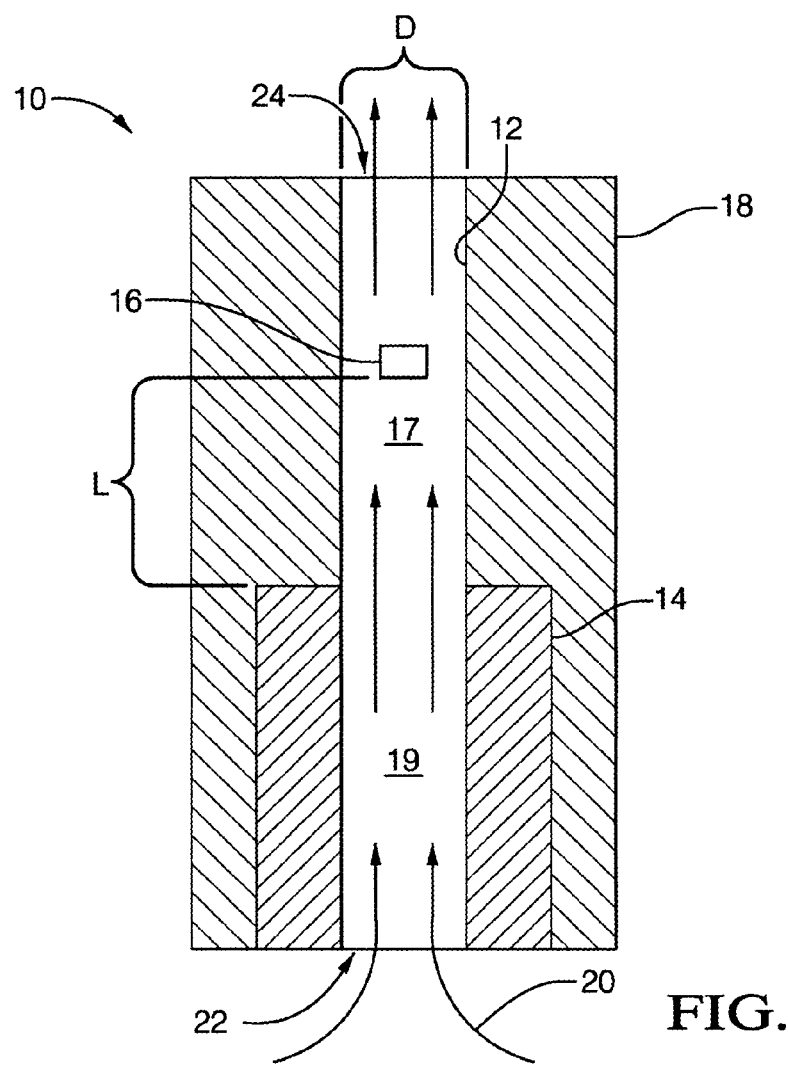
FIG. 1 illustrates an exemplary sectional view of a viscometer.

FIG. 1 illustrates an exemplary sectional view of a viscometer 10. Generally, the viscometer 10 includes a fluid flow channel 12, a heating element 14 disposed around at least an exterior portion of a fluid flow channel 12 near an inlet end 22, and a temperature sensor 16 positioned within the fluid flow channel 12 downstream of the heating element 14. The viscometer 10 operates on the convection principle that a fluid will rise in a direction opposite from a force of gravity when heated. Based on this principle, the inventors have innovatively created a very accurate, yet simple, inexpensive viscometer that may use a single temperature sensor 16 and does not rely on any moving parts. The flow channel 12 receives a fluid 20, such as oil, at an inlet end 22 and discharges the fluid 20 at an outlet end 24. In an aspect of the invention, the flow channel 12 may be tubular. In addition, the flow channel 12 may be formed from two different materials. For example, an upstream portion 19 of the flow channel 12, such as a portion surrounded by the heating element 14 may be formed from a relatively high thermally conductive material, such as copper or aluminum. A downstream portion 17 of the flow channel 12, such as a portion housing the temperature sensor 16, may be formed from a relatively low thermally conductive material. In a further aspect of the invention, a diameter, D, of the flow channel 12 may range between 2 millimeters (0.08 inches) and 3.5 millimeters (0.14 inches), for measuring fluids having a viscosity in the range of 10 millimeters$^2$/second to 60 millimeters$^2$/second. In yet another aspect, the flow channel 12 may have a constant inner diameter.

The heating element 14 heats a portion of the fluid 20 near the inlet end 22, causing the fluid 20 to flow in the flow guide 12 by convection. In one form, the heating element 14 may include heating wires wrapped around an exterior portion of the flow channel 12 near the inlet end 22. In another form, the flow guide 12 may include a ceramic tube with a heating element 14, for example, painted around a portion of the exterior of the ceramic tube near the inlet end 22. An aspect of the present invention that is particularly advantageous is the fact that the heating element 14 is arranged not to interfere with the fluid 20 flow that passes through the flow channel 12. This avoids or reduces the possibility of turbulence formation in the fluid 20 passing through the flow channel 12. Turbulence in the fluid 20 is not desirable since this could affect the accuracy of the viscometer 10. According to the convection principle, a lower viscosity fluid will flow away from the heating element 14 at a faster rate than a higher viscosity fluid, as the fluids are heated by the same amount. Accordingly, by monitoring temperature change of the fluid 20 over time, viscosity of the fluid 20 can be determined. To monitor the temperature of the fluid 20, the temperature sensor 16 is positioned within the fluid flow channel 12 downstream of the heating element 14 at a distance L, such as from 3 millimeters (0.12 inches) to 10 millimeters (0.4 inches), for measuring a temperature of the fluid 20 as it passes by the sensor 16. In an aspect of the invention, the temperature sensor 16 may be made as small as practical to prevent turbulence in the flow channel 12 near the sensor 16, which might affect a temperature measurement. For example, the temperature sensor 16 may be a resistive temperature device (RTD) having a length of approximately 2 millimeters (0.08 inches), and a width and depth of approximately 0.5 millimeters (0.02 inches), and having a low thermal mass, or a relatively fast temperature response time such as 0.1 second. By measuring the temperature of the fluid flowing through the fluid flow channel 12 over time, the viscosity of the fluid 20 can be determined by comparing recorded temperature change characteristics to temperature change characteristic for known fluid viscosities as may be stored in a database.

In one aspect of the invention, the viscometer 10 may be immersed in the fluid 20 so that the inlet end 22 generally points towards the Earth's center of gravity and an outlet end 24 points away from the Earth's center of gravity. Accordingly, a heated fluid 20 rises in the fluid flow channel 12 away from the heating element 14 towards the temperature sensor 16 in a direction opposite from the force of Earth's gravity. For example, the viscometer may be immersed in an oil pan of an engine in an orientation aligned with the force of Earth's gravity, such as vertically in the oil pan. The viscometer 10 may also include a thermally insulating jacket 18 disposed around the heating element 14 and the fluid flow channel 12. The insulating jacket serves to limit heat transfer from a portion of the fluid 20 flowing in the flow channel 12 and the portion of the fluid 20 outside of the flow channel 12.

A method of operating the viscometer 10 to determine a viscosity of a fluid 20, such as oil, may include initially immersing the viscometer in the fluid 20 so that the fluid 20 fills the fluid flow channel 12. A portion of the fluid 12 near the inlet end of the fluid flow channel 12 is then heated. As the heated fluid 20 rises, the temperature of the fluid 20 in the fluid flow channel 12 is measured at a position downstream from the inlet end 22 of the flow path. The temperature changes of the fluid 20 are then recorded for a time period and the recorded temperature change characteristics are compared to temperature change characteristics for known fluid viscosities to establish the viscosity of the fluid 20. For example, to measure the viscosity of a lubricated component in a vehicle, such as in a land vehicle, a watercraft, or an aircraft, the viscometer is immersed in the lubricant, vertically with respect to the force of gravity. In one form, viscosity is measured while the vehicle is in a non-operational state. The lubricant may be allowed to cool down to a desired temperature after an operating period. For example, engine oil may be allowed to cool down to 70 degrees centigrade before performing a measurement. When the lubricant has cooled down to the desired temperature, the heating element 14 may be turned on, such as by applying an energizing voltage to the element to achieve a constant power output of the heating element 14, to heat a portion of the lubricant near the inlet 22 of the fluid flow channel 12.

The inventors have experimentally observed that the duration of the heat applied and the amount of temperature change imparted to the flow 20 may affect the temperature measurement. For example, if the heating element 14 is allowed to apply relatively excessive heat to the fluid, turbulence in the flow channel 12 may be created due to the excessive heating. This could result in inaccurate temperature readings. Conversely, if the fluid 20 is not heated enough, the fluid 20 may rise too slowly in the flow channel 12 and may lose heat while traveling from the vicinity of the heating element 14 to the temperature sensor 16. Accordingly, in one exemplary embodiment, the heating element 14 may be powered for approximately 2 to 3 minutes, and may be provided with an appropriate amount of power to raise the temperature of the lubricant in the vicinity of the heating element 14 approximately five to ten degrees centigrade higher than the desired temperature to achieve repeatable results.

The inventors have also experimentally observed that the distance L between the heating element and the temperature sensor 16 may affect temperature reading repeatability. For example, if the temperature sensor 16 is too close to the heating element 14, the heat transfer may occur along the walls of the flow channel 12. Conversely, if the temperature sensor 16 is mounted too far away from the heating element 14, the fluid may loose some heat to the flow channel 12 while traveling from the vicinity of the heating element 14 to the temperature sensor 16. Accordingly, in one exemplary embodiment, the temperature sensor 16 may be positioned approximately 3 to 10 millimeters away from the heating element 14 to achieve repeatability in temperature measurements.

Figure 3:
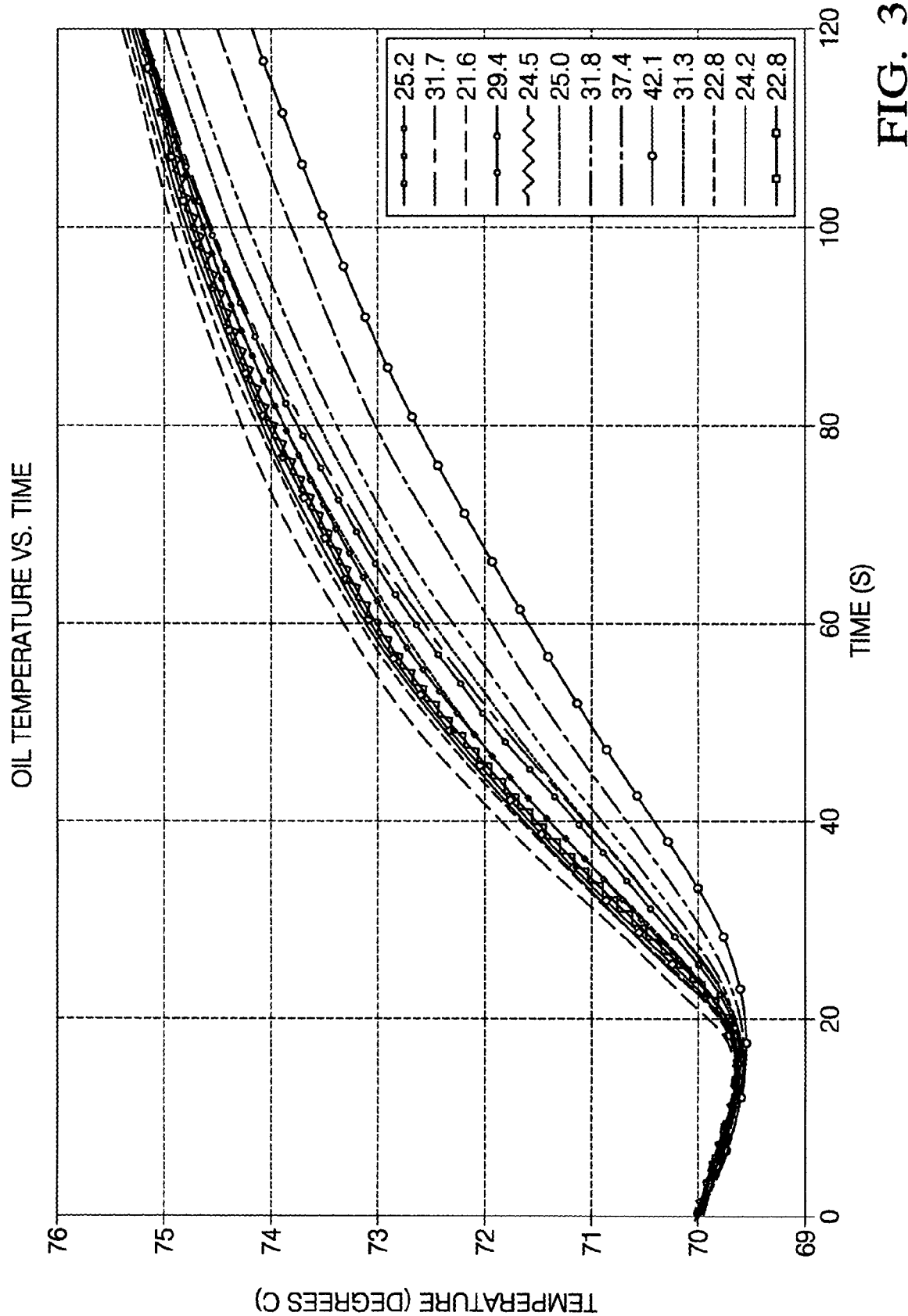
FIG. 3 is an exemplary graph of oil temperature versus time of heating curves for various oil viscosities of fresh oils.
Figure 4:
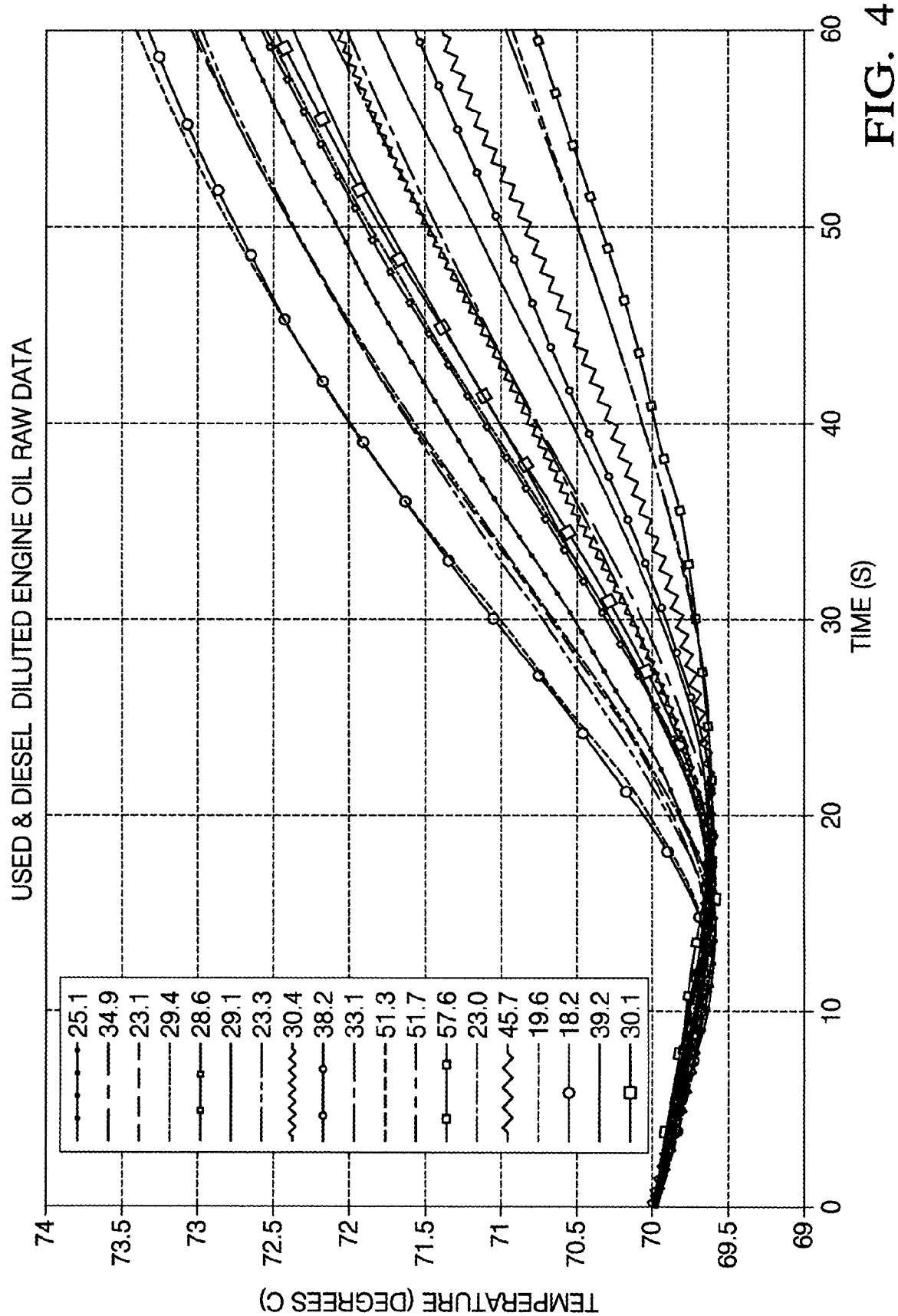
FIG. 4 is an exemplary graph of oil temperature versus time of heating curves for various oil viscosities of used oils.
Figure 5:
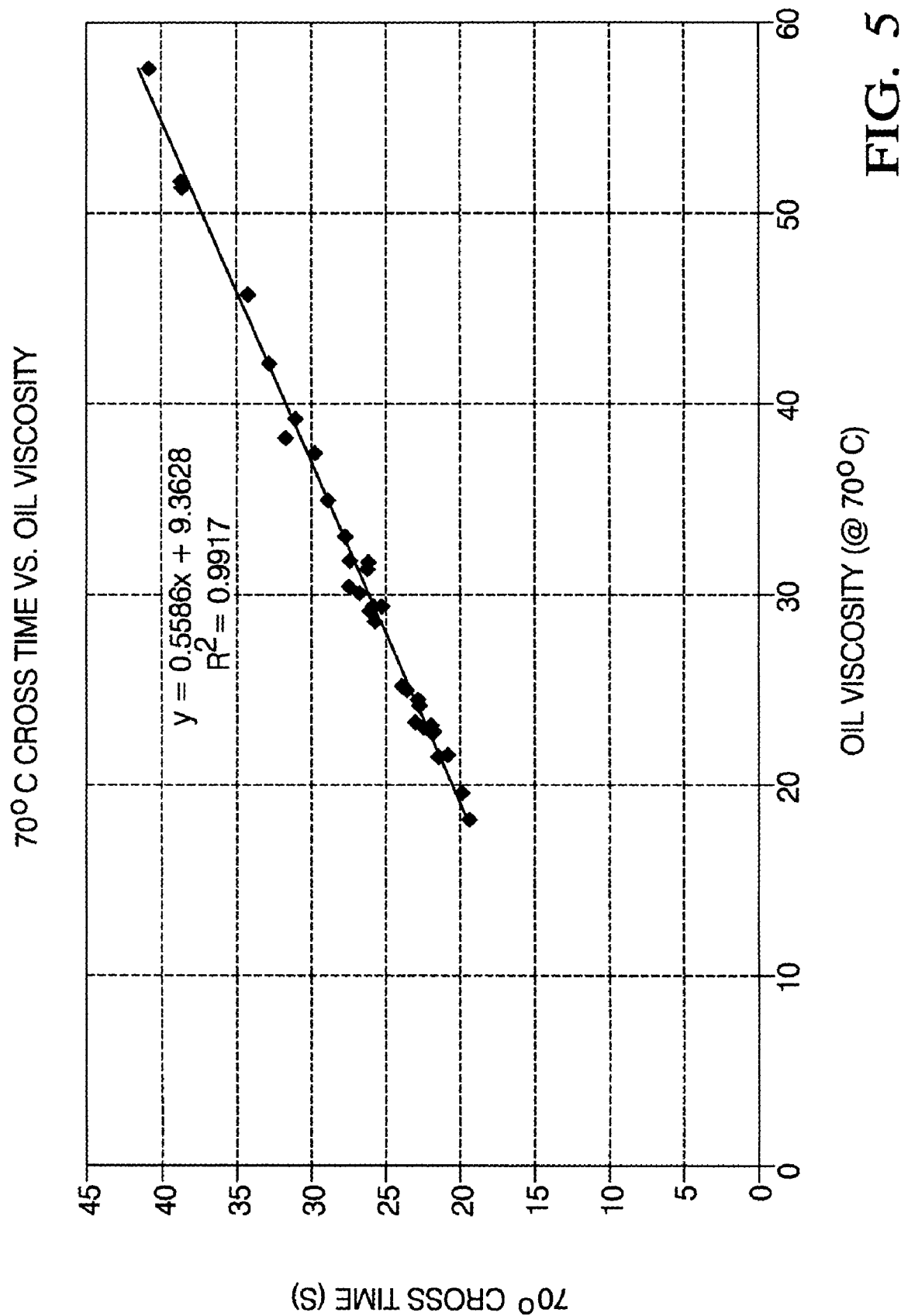
FIG. 5 is an exemplary graph of the times at which each of the oil viscosity heating curves shown in FIGS. 3 and 4 cross the 70 degrees temperature axis of FIGS. 3 and 4 versus a viscometer output index for various oil viscosities.

Once the temperature measurements have been recorded over time, the recorded temperature change characteristics can be compared to temperature change characteristic for known fluid viscosities to establish the viscosity of the fluid 20. For example, FIGS. 3 and 4 are exemplary graphs of oil temperature versus time for various oil viscosities measured and plotted using the viscometer 10 of the present invention. FIG. 5 is an exemplary graph of the times at which each of the oil viscosity heating curves shown in FIGS. 3 and 4 cross the 70 degrees temperature axis of FIGS. 3 and 4 versus a viscometer output index for various oil viscosities. A viscosity index for a respective oil may be calculated by integrating the corresponding plotted viscosity curve over time to obtain an area under the viscosity curve that is proportional to the viscosity of the oil.

By comparing the known temperature change characteristics of the oil viscosities shown in FIGS. 3 and 4 to recorded temperature change characteristics of a tested oil, the viscosity of the tested oil can be established by determining how well the tested oil temperature characteristics match the temperature characteristics of a known oil viscosity. For example, a calculated index for a tested oil may be compared to an index for a known oil viscosity to determine if the indexes match. If the indexes match, then the viscosity of the tested oil is the same as the known oil.

Figure 2:
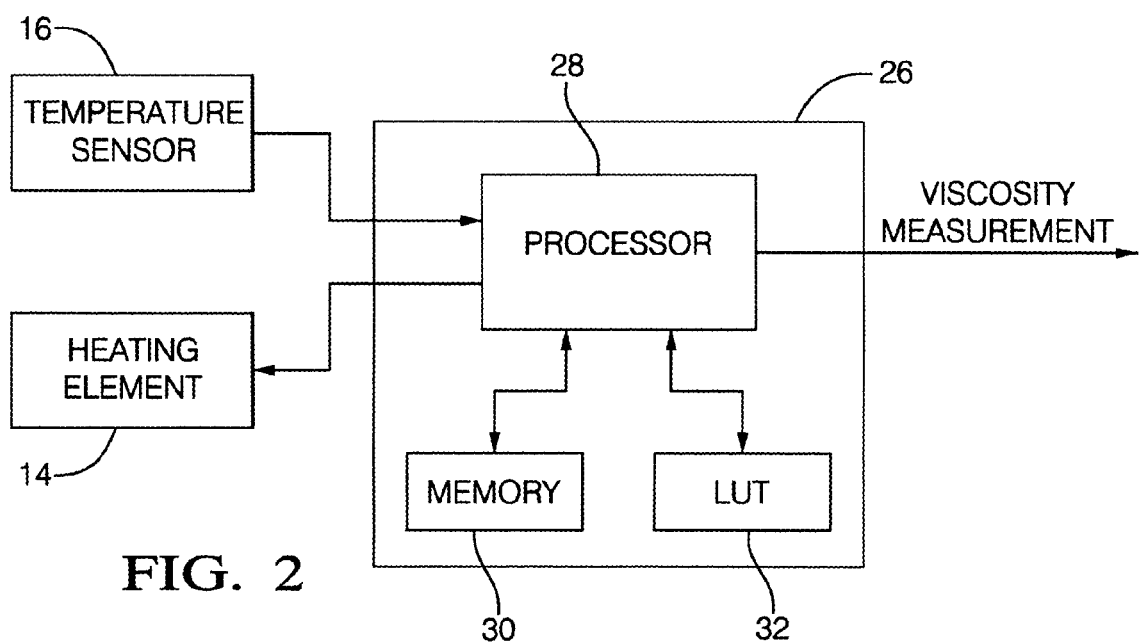
FIG. 2 is a block diagram representation of one exemplary embodiment of a controller for the viscometer of FIG. 1.

To provide a viscosity measurement, the viscometer 10 may also include a controller 26 as shown in FIG. 2. Generally, the controller 26 includes a processor 28 for regulating the heating element 14 and reading the temperature sensor 16. For example, the processor may be a microprocessor or a custom processing device, such as a reconfigurable algorithm processor (RAP). The processor 28 may be configured to control the time duration that the heating element 14 is turned on and control the power applied to the heating element 14 for making a viscosity measurement. The controller 26 may further include a memory 30 for storing temperature readings from the temperature sensor 16, and a look up table (LUT) 32 or database for storing temperature characteristics for known fluid viscosities. The processor 32 can compare the characteristics of temperature readings over time stored in memory 30 to known temperature characteristics for fluid viscosities to establish the viscosity of the fluid based on the comparison.

The method of the present invention can be embodied in the form of computer-implemented processes and apparatus, such as embedded processors, for practicing those processes. The present invention can also be embodied in the form of computer program code containing computer-readable instructions embodied in tangible media, such as RAM, floppy diskettes, CD-ROMs, hard drives, or any other computer-readable storage medium, wherein, when the computer program code is loaded into and executed by a computer or processor, the computer or processor becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a processor, the computer program code segments configure the processor to create specific logic circuits or processing modules.

While the preferred embodiments of the present invention have been shown and described herein, it will be obvious that such embodiments are provided by way of example only. Numerous variations, changes and substitutions will occur to those of skill in the art without departing from the invention herein. For example, the viscometer may be used in any type of component having a fluid associated with the operation of the component, or may used in a stand alone situation where the viscosity of a fluid is desired to be known. The invention has application in measuring viscosity of lubricants, for example, in land vehicles, watercraft, and aircraft. The small size, relative simplicity, and relative inexpense of the viscometer allow it to be used in a variety of components, including lubricated components such as in internal combustion engines, transmissions, and hydraulic systems. Accordingly, it is intended that the invention be limited only by the spirit and scope of the appended claims.

The invention claimed is:

1. A viscosity measurement apparatus comprising:
a fluid flow channel;
wherein the fluid flow channel further comprises:
an upstream portion comprising a comparatively high thermally conductive material; and
a downstream portion comprising a comparatively low thermally conductive material
a heating element arranged at least around an exterior portion of the fluid flow channel proximate an inlet end; and
a temperature sensor disposed within the fluid flow channel downstream from the heating element, wherein the arrangement of the heating element relative to the fluid flow channel reduces a possibility of turbulence formation in a fluid passing therethrough.

2. The apparatus of claim 1, wherein the upstream portion comprises a metal selected from the group consisting of copper and aluminum.

3. An oil viscosity measurement system for internal combustion engines comprising:
a tubular flow guide for receiving oil at an inlet end and discharging the oil at an outlet end;
a heating element disposed around an exterior portion of the tubular flow guide proximate the inlet end for heating oil entering the inlet end, whereby said oil is not moved through said tubular flow guide by any external force, but by convection created by said heating element; and
a temperature sensor disposed within the tubular flow guide proximate the outlet end for measuring a temperature of oil proximate the sensor.

4. The system of claim 3, further comprising an insulating jacket disposed around the heating element and the tubular flow guide for reducing heat transfer between a first portion of oil located in the tubular flow guide and a second portion of oil outside the tubular flow guide.

5. The system of claim 3, wherein the tubular flow guide comprises a constant inner diameter from approximately 2 millimeters (0.08 inches) to approximately 3.5 millimeters (0.14 inches) along a length of the flow guide.

6. The system of claim 3, wherein the temperature sensor is positioned from approximately 3 millimeters (0.12 inches) to approximately 10 millimeters (0.4 inches) from the heating element.

7. The system of claim 3, further comprising a controller for regulating the heating element and reading the temperature sensor.

8. The system of claim 7, wherein the controller further comprises:
a memory for storing temperature readings from the temperature sensor; and
a processor for comparing characteristics of the stored temperature readings over time to temperature characteristics for known oil viscosities to determine the viscosity of the oil.

9. The system of claim 7, further comprising a look up table for storing the temperature characteristics for the known oil viscosities.

10. A method for measuring viscosity of a fluid comprising:
immersing a fluid flow channel in the fluid;
heating a portion of the fluid in the fluid flow channel proximate an inlet end of the fluid flow channel; and
measuring a temperature of the fluid in the fluid flow channel at a position downstream from the inlet end of the fluid flow channel.

11. The method of claim 10, further comprising orienting the fluid flow channel in a direction parallel to a force indicative of Earth's gravity.

12. The method of claim 10, further comprising:
recording temperature changes of the fluid for a time period; and
comparing recorded temperature change characteristics to temperature change characteristics for known fluid viscosities to determine the viscosity of the fluid.

13. The method of claim 10, further comprising heating the fluid from approximately 2 to approximately 3 minutes.

* * * * *